United States Patent [19]

LaFond

[11] Patent Number: 4,563,175

[45] Date of Patent: Jan. 7, 1986

[54] MULTIPLE SYRINGE PUMP

[76] Inventor: Margaret LaFond, R.R. 2 - Box 219-L15, Kankakee, Ill. 60901

[21] Appl. No.: 562,910

[22] Filed: Dec. 19, 1983

[51] Int. Cl.$^4$ .............................................. A61M 5/00
[52] U.S. Cl. .................................... 604/155; 604/191; 604/246; 128/DIG. 12
[58] Field of Search ............... 604/152, 154, 155, 191, 604/246; 128/DIG. 12

[56] References Cited

U.S. PATENT DOCUMENTS

| 3,949,746 | 4/1976 | Wallach | 604/152 |
| 4,044,757 | 8/1977 | McWhorter | 604/124 X |
| 4,065,230 | 12/1977 | Gezari | 604/152 X |
| 4,191,187 | 3/1980 | Wright | 604/155 |
| 4,196,730 | 4/1980 | Wilson | 604/155 |
| 4,255,096 | 3/1981 | Coker, Jr. et al. | 604/152 X |
| 4,435,173 | 3/1984 | Siposs et al. | 604/155 |

*Primary Examiner*—Stephen C. Pellegrino
*Attorney, Agent, or Firm*—Ernest Kettelson

[57] ABSTRACT

A multiple syringe pump, comprising a pump housing, two or more seating recesses therein to receive two or more syringes for delivering two or more different substances to a patient intravenously, such as nutritional elements in one and medication substances in another, and a corresponding plurality of drive mechanisms in said pump housing powered by an electrical source for connection to each of the two or more syringes seated in said pump housing to move the syringe plungers at a controlled rate in the direction to discharge the contents of the syringe cylinder. The discharge ports of the syringes are connected to respective discharge tubes which in turn lead to a Y-connector which has its common outlet port connected to a single tube leading to a patient for intravenous infusion of the respective substances. The seating recesses of the pump housing are of different sizes to accept different sized syringes. The drive mechanisms are operable and controllable separately, for operation at different rates of speed and to independently control rates of discharge of the contents of each of the syringes.

16 Claims, 5 Drawing Figures

MULTIPLE SYRINGE PUMP

BACKGROUND OF THE INVENTION

This invention relates to the field of medical devices known as syringe pumps, in which a syringe is placed with its plunger connected by a plunger clamp to the drive mechanism of the pump which pushes the plunger inwardly of the syringe barrel or cylinder at a controlled rate to force the contents of the syringe out at a controlled rate into tubing which leads to a patient being fed or infused intravenously.

Prior art devices of this type have either had provision for only one syringe, or for two syringes of the same size to be operated by the same drive mechanism at the same rate. The present invention provides seating recesses for two or more syringes of different sizes, and a corresponding number of independently operable drive mechanisms to control the outward flow from each syringe independently and at different rates of flow. In this way, nutritional elements which require a larger syringe cylinder or barrel can be fed at one rate of flow while medicinal substances for which smaller syringes are more appropriate can be fed at a different rate of flow. A third syringe can also be provided for in accordance with this invention to flush out the lines, having a separate third driving mechanism and separate control to regulate the time and rate of operation of the third syringe. This invention is primarily for use in the care of infants who require intravenous feeding or infusion.

Examples of prior art devices in this field are disclosed in the following U.S. patents.

U.S. Pat. No. 4,359,049 discloses a double syringe holder for operating two syringes simultaneously by hand.

U.S. Pat. No. 4,243,030 discloses a two syringe-like device for implanting into animals and infusing substances at different time intervals to observe the reaction of the animal to each of the different infusions.

U.S. Pat. No. 4,109,653 discloses a double barrel type of syringe for operation by hand.

U.S. Pat. No. 4,098,275 discloses a Y-connector for connection of a common outlet lead and needle to two separate supply sources for infusion into a patient's arm.

U.S. Pat. No. 4,044,757 discloses a pair of syringes of the same size mounted together in a holding device for manual operation, the syringes being connected at their outlet ends to a common outlet tubing by a manifold type connector.

U.S. Pat. No. 2,564,977 discloses a medical injecting apparatus having two syringes connected to a common needle.

U.S. Pat. No. 2,112,160 discloses a syringe-like medical device having two chambers or barrels connected to a common outlet tube by a Y-type connector.

U.S. Pat. No. 1,948,388 discloses a syringe device having a triple outlet.

None of the prior art devices discloses a syringe pump mechanism in which a pluarlity of different size syringes can be mounted and connected to separate electrically powered driving mechanisms for independently controlling the flow rate of each syringe into a common tube leading to an infant being fed or infused intravenously by the device.

DESCRIPTION OF PREFERRED EMBODIMENT

Figure 1:
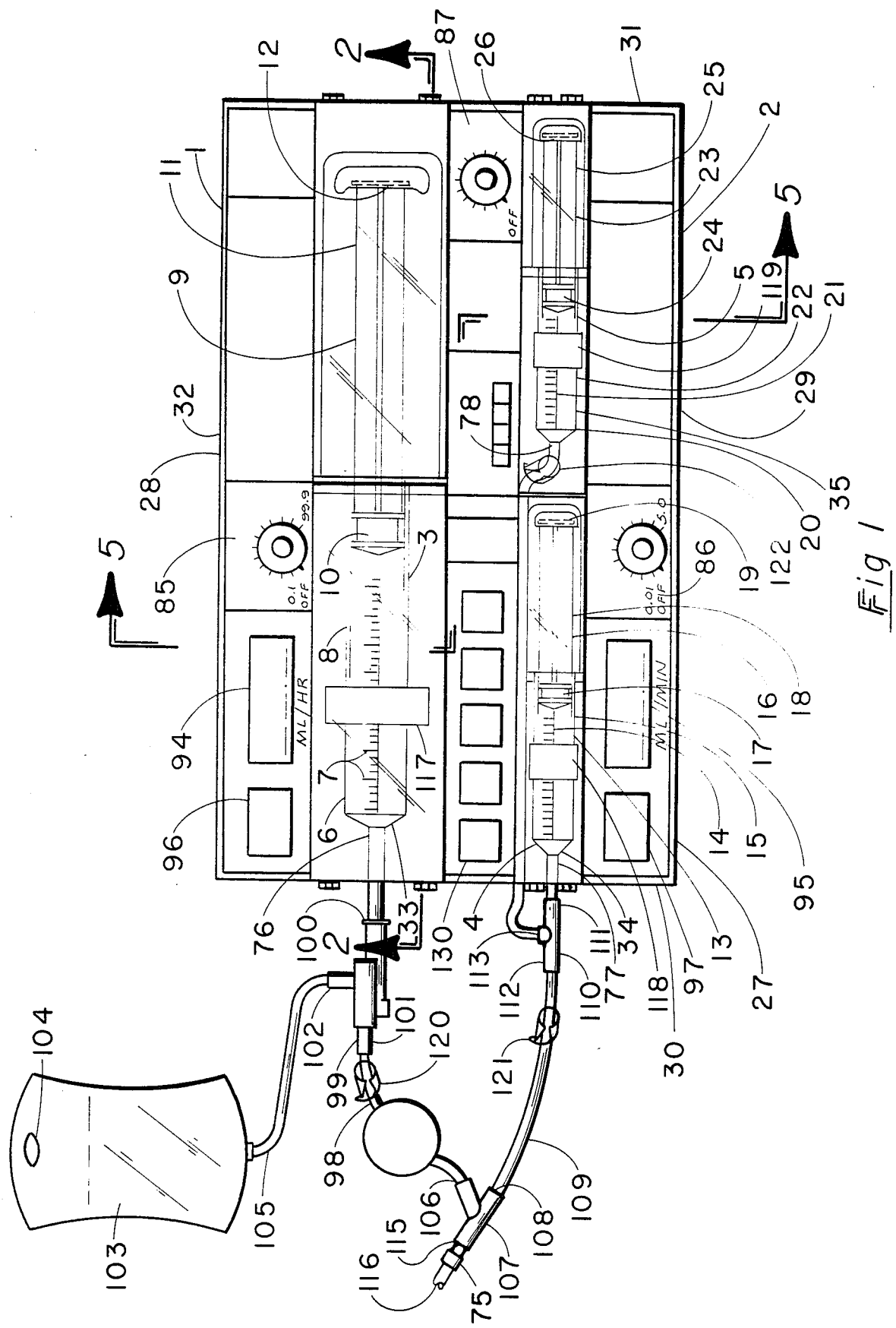
FIG. 1 is a perspective view of a syringe pump in accordance with this invention with three syringes mounted for operation therein.
Figure 2:
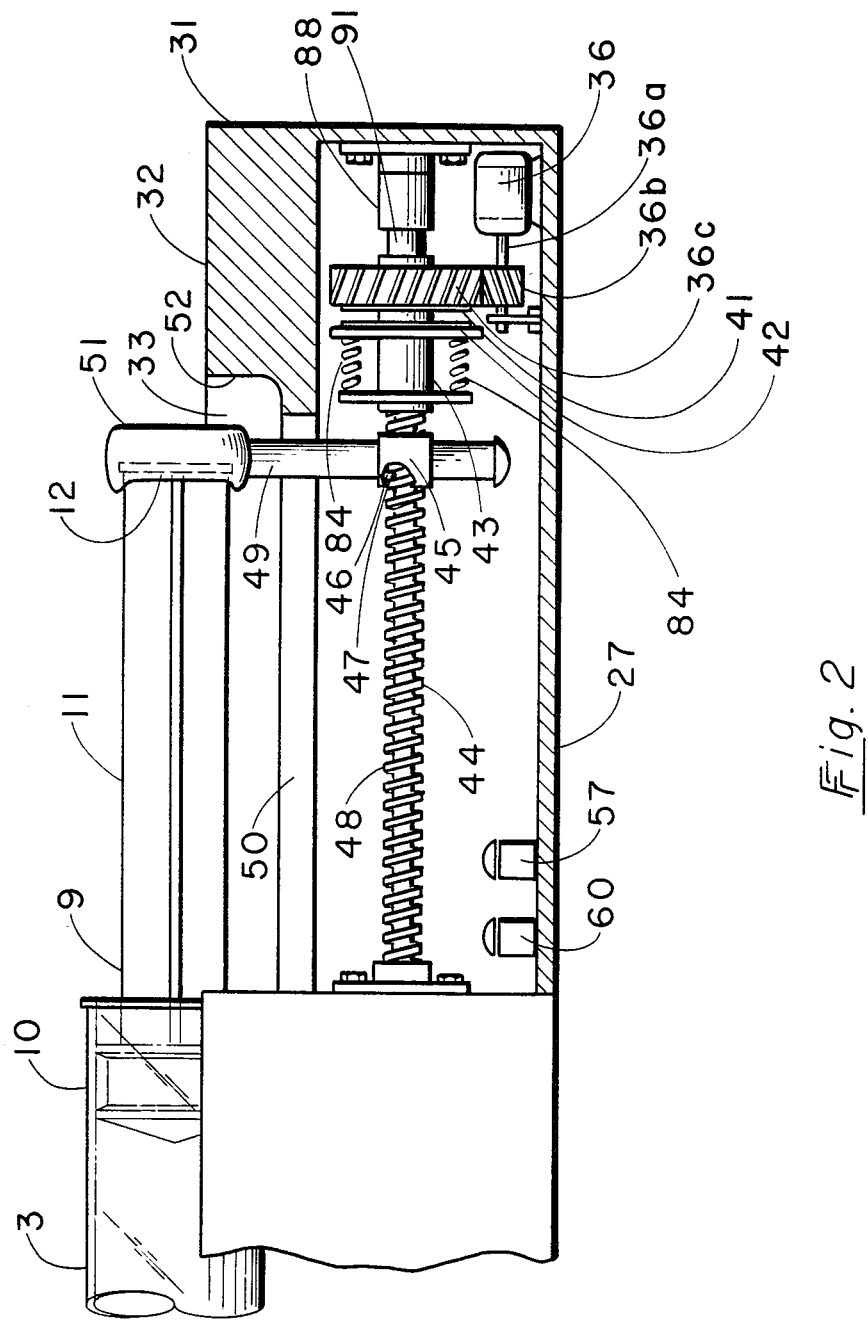
FIG. 2 is a side elevation view of one of the driving mechanisms of the syringe pump in accordance with this invention.
Figure 3:
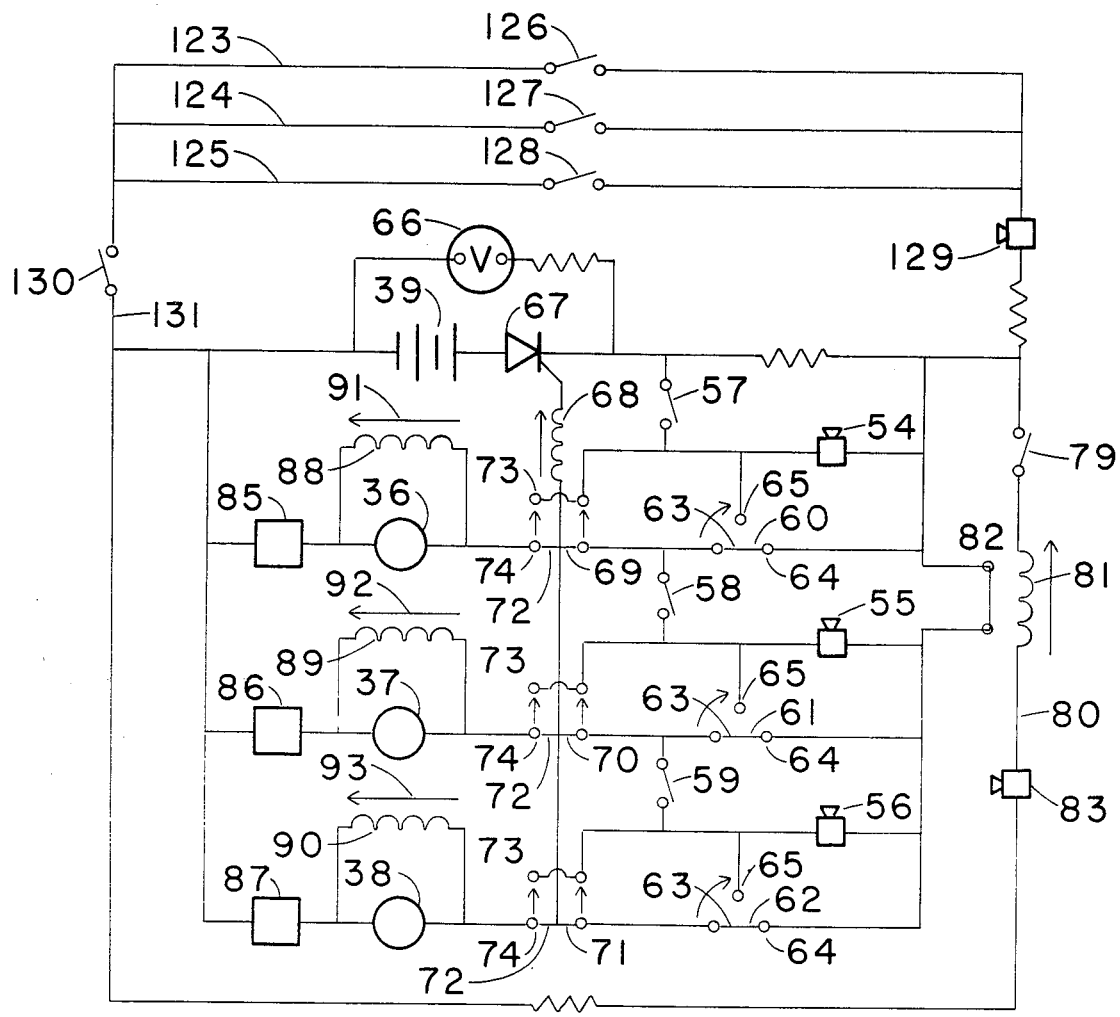
FIG. 3 is a schematic showing the electrical circuitry which powers the driving mechanism and other components of the syringe pump inaccordance with this invention.
Figure 4:
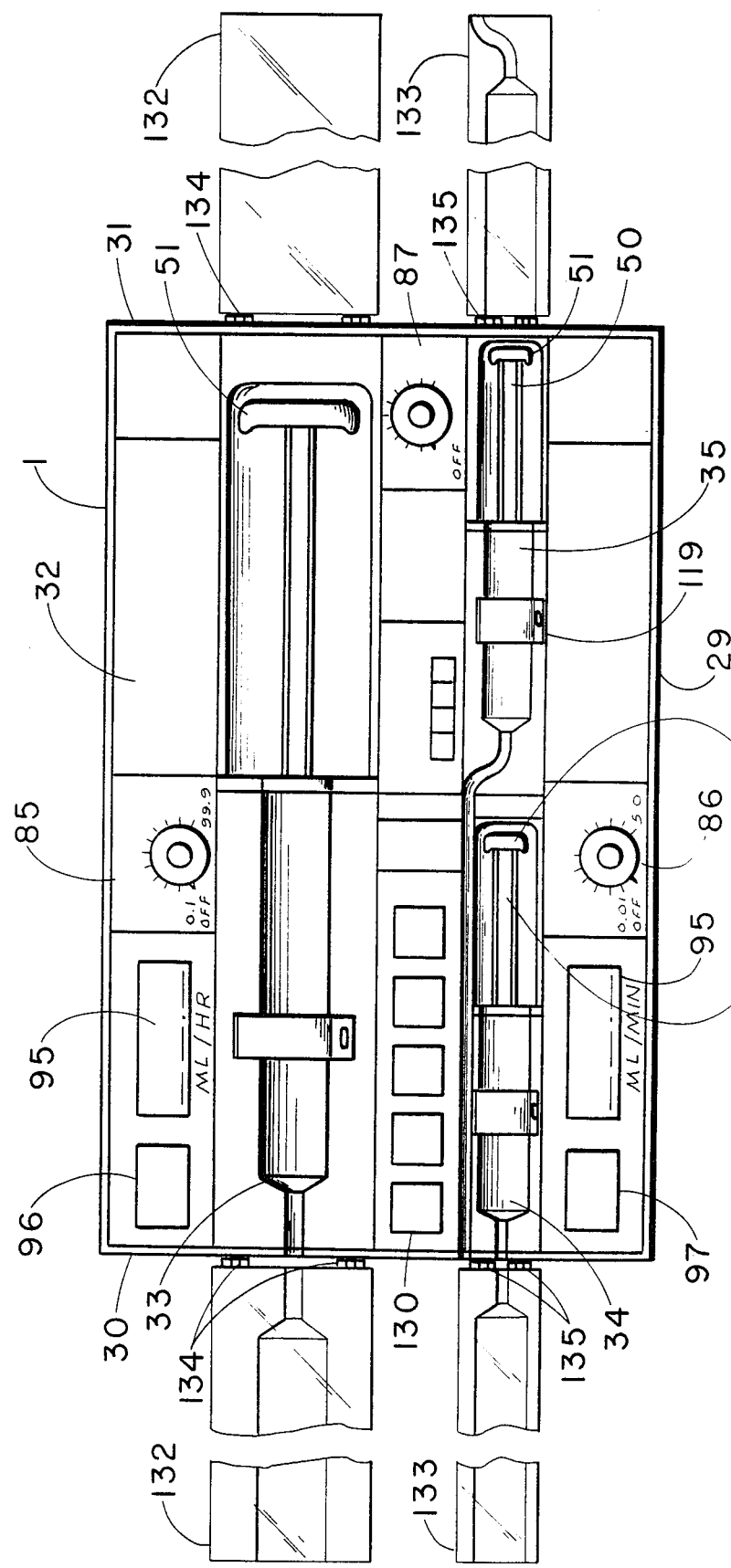
FIG. 4 is a plan view of the syringe pump shown in FIG. 1, but with the syringes removed.
Figure 5:
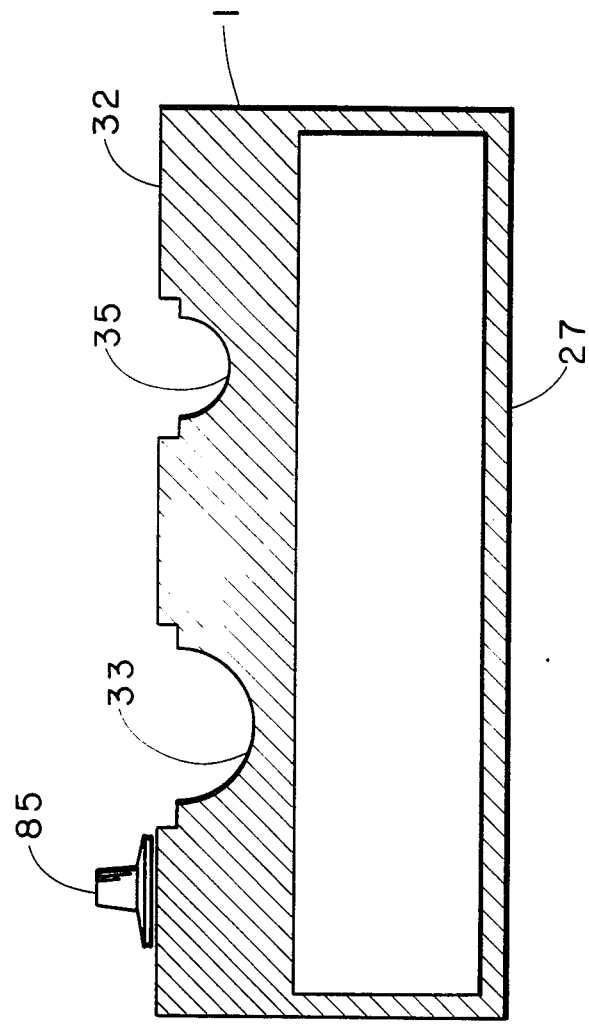
FIG. 5 is a section view taken on line 5—5 of FIG. 4.

The syringe pump 1 in accordance with this invention includes a housing 2 in which a large syringe 3 and a smaller syringe 4 are received for connection to separate individually controllable drive mechanisms to separately and independently control the outward rate of flow from each syringe 3 and 4.

A third syringe 5 is also provided, which is connected to a third separate individually controllable drive mechanism, for purposes of flushing out the lines of the infusion system.

The large syringe 3 is primarily for nutritional elements, and includes a large diameter cylindrical container 6 having quantity markings 7 along its side wall 8, a plunger 9 therein having a piston 10 inside of the cylindrical container 6 connected to a plunger rod 11 which extends outwardly from the cylindrical container 6 terminating in a plunger cap 12.

The smaller syringe 4 is primarily for medication substances, and includes a smaller diameter cylindrical container 13 having quantity markings 14 along its side wall 15, a plunger 16 therein having a piston 17 inside of the cylindrical container 13 connected to a plunger rod 18 which extends outwardly from the cylindrical container 13 terminating in a plunger cap 19.

The flushing syringe 5 is provided for filling with a normal saline solution to flush out the lines which lead from the nutritional element syringe 3 and the medication substance syringe 4 to the infant being fed intravenously. Flushing is necessary for reasons such as the following. The nutritional elements are not always compatible with the medication substances, for example a 10% dextrose nutritional solution is not compatible with a medication such as ampicillin, resulting in possible precipitation or solidifying within the lines. Therefore after infusion of the medication, the lines should be flushed out with a saline solution which may be done without removing the catheter from the baby who is being fed intravenously. This is the function of the flushing syringe 5, which includes a relatively small diameter cylindrical container 20 having quantity markings 21 along its side wall 22, a plunger 23 therein having a piston 24 inside of the cylindrical container 20 connected to a plunger rod 25 which extends outwardly from the cylindrical container 20 terminating in a plunger cap 26.

The housing 2 includes a rectangular box having a botom wall 27, a pair of oppositely disposed long side walls 28 and 29, a pair of oppositely disposed short end wall 30 and 31 connected respectively to the side walls 28 and 29 at opposite ends, and a top wall 32.

The top wall 32 includes three molded seating recesses formed to conform to the side wall configuration and dimension of respective ones of the three syringes, large seating recess 33 for the nutritional syringe 3, smaller seating recess 34 for the medication syringe 4, and a relatively small seating recess 35 for the flushing syringe 5.

The length of the nutritional syringe 3 is also greater than that of the medication syringe 4 and flushing syringe 5, being about twice as long in the embodiment shown in the drawing and described herein. Thus, in this embodiment, the nutritional syringe 3 lies in a seating recess which extends for substantially the length of the longest side of housing 2, the cylindrical container 6 taking up about half of such length and the plunger rod 11 taking up the other half when fully extended.

The medication syringe 4 and flushing syringe 5 lie in seating recesses 34 and 35 which are axially aligned, and substantially parallel to the large seating recess 33 in which the nutritional syringe 3 is received. Thus, when medication syringe 4 and flushing syringe 5 are received in their respective seating recesses 34 and 35 theyare in substantially axial alignment with each other, and substantially parallel to nutritional syringe 3.

The top wall 32 of the housing 2 also includes the controls, indicators and alarms described herein below.

Each syringe 3, 4 and 5 is connected to and operated by three separate driving mechanisms, each separately operable and controllable. The driving mechanisms are substantially identical except for variations in size, so the mechanism for only one of them will be described in detail. Each if driven by separate electric motors 36, 37 and 38, all three of the motors connected in a circuit powered by a battery 39, and the operation of each motor is controlled by respective variable speed controllers. The driving mechanism connected to motor 36 for operating the large nutritional syringe 3 will be described in detail.

The motor 36 includes a drive shaft 36a having a small spur gear 36b mounted therein for engagement with a relatively large spur gear 36c. A friction clutch 40 is provided, having a friction drive plate 41 bolted to the outwardly facing side wall of the large spur gear 36c and a frictionally driven plate 42 mounted on clutch shaft 43 for short reciprocal movment between a disengaged position in which it is away from and out of contact with the drive plate 41 and an engaged position in which it is against the drive plate 41 in frictional driving contact therewith. The clutch shaft 43 is integrally connected to an elongated worm gear 44 for rotation thereof when the clutch 40 is in its engaged position and the motor 36 is energized.

A drive member 45 is mounted on the worm gear 44, having a central bore 46 through which the worm gear 44 is received, and an internal helical groove 47 of said bore which receives the corresponding external helical rib 48 of the worm gear 44 for driving engagement therewith. The drive member 45 includes an upwardly extending arm 49 which projects through an elongated slot 50 in the top wall 32 of the housing 2, and which extends along the longitudinal midline of the seating recess 33 for that part of its length which corresponds to the travel of plunger rod 11 of syringe 3 when seated in said recess between its fully extended position and its fully retracted or depressed position. A plunger clamp 51 is provided at the outer end of arm 49 of drive member 45 for clamping over the plunger cap 12 of the plunger rod 11 of the nutritional syringe 3.

When the worm gear 44 is rotated by the motor 36, the drive member 45 is thus moved longitudinally along the slot 50 from the outer end 52 of seating recess 33 toward its midpoint whereby the plunger rod 11 with its cap 12 grasped by the plunger clamp 51 of drive member 45 is moved from its extended position toits retracted or depressed position. As it is moved inwardly, the piston 10 pushes the nutritional element contents of syringe 3 outwardly into the lines leading to the infant being fed intravenously. The rate of outflow can be controlled by the variable speed controller 85 which controls the operation of the electric motor 36.

The driving mechanisms connected to motors 37 and 38 for feeding out the contents of medication syringe 4 and the flushing syringe 5 operate in the same way and include substantially identical parts and structure differing only in size.

When any one of the syringe vials or cylindrical containers 6, 13 and 20 of the respective syringes 3, 4 and 5 are emptied to the point only one millimeter of their respective contents remain, respective audible alarms 54, 55 and 56 sound respectively, and when the vials or cylindrical containers are completely empty the respective alarms for such syringes again give an audible sound and the respective motors 36, 37 and 38 which operate the respective syringes that have reached the empty mark automatically stop.

The operation of these alarms at the one millileter and empty levels, and automatic stop at the empty level is as follows.

When the piston of each respective syringe (piston 10 for syringe 3, piston 17 for syringe 4, and piston 24 for syringe 5) reaches the marking of one millileter on the side wall of its respective vial or container, the respective member 45 which is driving each respective piston contacts respective ones of first limit switches 57, 58 and 59. Such limit switches which are normally open, then close to complete a circuit through the particular alarm 54, 55 or 56 which is associated with the syringe that has reached the one millileter level. At this time, the respective motor does not stop but continues driving the plunger until its piston 10, 17 or 24 reaches the empty mark on the side wall of the syringe vial. When this point is reached by the piston, the corresponding drive member 45 then contacts respective ones of second limit switches 60, 61 and 62. Such limit switches which are also normally open in the alarm circuit, then close to complete a circuit through the particular 54, 55 or 56 which indicates that syringe 3, 4 or 5 has reached the empty mark.

The limit switches 60, 61 and 62 are bi-polar, the movable contact 63 being normally biased to a closed contact position with stationary contact 64 in the motor energizing circuit and out of contact with stationary contact 65 in the alarm circuit. When anyone of the limit switches 60, 61 and 62 are contacted by the respective drive member 45 which is operating the syringe such limit switch is associated with, the movable contact 63 is moved to the closed contact position with stationary contact 65 in the alarm circuit thereby energizing the alarm circuit, and out of contact with the stationary contact 64 in the motor circuit thereby interruptingthat circuit and automatically stopping the motor when the syringe it is operating becomes empty.

A third audible alarm is provided to indicate when the battery 39 beings to weaken. A voltmeter control 66 is connected in a circuit with an electronic switch, SCR 67 which switches current through solenoid 68 when battery power falls below a predetermined voltage. The solenoid 69 operates three bipolar switches 69, 70 and 71 which are connected to sequentially open and close (1) the alarm circuits which energize the audible alarms 54, 55 and 56 and (2) the motor circuits which energize the motors 36, 37 and 38. Each of the bipolar switches 69, 70 and 71 include a movable contact arm 72 and two stationary contacts 73 and 74. Stationary contact 73 are in the alarm circuit and stationary contacts 74 are in the motor circuit of each of the three alarm and motor circuits. The bipolar switches are normally biased to the position in which movable contact arms 72 are in closed contact position with stationary contacts 74 in the motor circuits for operating the motors 36, 37 and 38 when those circuits are energized. When the voltage of battery 39 falls below its rated voltage a preselected amount, the voltmeter control 66 in circuit with SCR 67 signals the SCR to direct current through solenoid 68. When solenoid 68 becomes energized it draws movable contact arms 71 from stationary contacts 74 thereby interrupting the motor circuits causing all three motors 36, 37 and 38 to stop, and draws movable contact arms 71 into closed position with stationary contacts 73 in the alarm circuits. All three alarm circuits are then energized and all three of the audible alarms 54, 55 and 56 then emit an audible sound to indicate that battery power has dropped below the pre-determined level at which it can operate to feed substances from the syringes at the accurately controlled rate required.

A fourth audible alarm is provided to indicate if and when there is any interruption of the flow from the syringes. Such alarm works as follows. A pressure sensitive valve 75 is connected in the feed line between (1) the outlet 76, 77 and 78 of the respective syringes 3, 4 and 5 and (2) the infant or other patient to whom the intravenous feed lines are connected. In the event of any blockage in the line, or of any back pressure in the line, or of any drop of pressure in the line, either above or below the normal flow pressure that should be in the line, the pressure sensitive valve 75 closes limit switch 79 in a pressure control circuit 80 connected between the pressure sensitive valve 75 and the battery circuit. When limit switch 79 completes the pressure control circuit 80, solenoid 81 becomes energized to cause motor circuit master switch 82 to open thereby interrupting the entire motor circuit causing all three of the motors 36, 37 and 38 to stop if their individual sub-circuits had been energized and if they had been operating. The pressure control circuit 80, includes a separate audible alarm 83 which also sounds when limit switch 79 closes to complete pressure control circuit 80 indicating that a change of pressure has occured in the feed lines requiring that the entire device be shut down.

The friction clutch 40 of each of the three drive mechanisms has its driven plate 42 normally biased toward the disengage position by compression springs 84. If no current is flowing in the particular sub-circuit that provides electrical power to motors 36, 37 and 38, the driven plate 42 of clutch 40 is in the disengage position. Each motor sub-circuit is controlled by motor controllers 85, 86 and 87, which not only close or complete and open or interrupt each sub-circuit that energized or de-energizes motors 36, 37 and 38 but they also vary and control the speed at which each motor operates. When the motor controllers are moved to a position which energize their particular circuit, current is directed through clutch operating solenoids 88, 89 and 80 which move solenoid cores 91, 92 and 93 in a direction opposite to that of the bias of the compression springs 84. The driven plates 42 are connected to the springs 84 and solenoid 88, 89 and 90, so when the solenoids are energized they draw the clutch plates 42 into driving engagement with the drive clutch plate 41 against the bias of the syringe 84. When the motor circuits are interrupted, either by moving the motor controllers to the "off" position, or by a syringe becoming empty, or by an unacceptable increase or decrease of pressure in the lines leading from the syringes, the solenoids 88, 89 and 90 are de-energized thus allowing the springs 84 to bias the driven clutch plates 42 away from the drive clutch plates 41 thereby disengaging the clutch 40 and disconnecting the worm gear 44 of the driving mechanism from its respective motor 36, 37 and 38.

When the worm gear 44 is disconnected from the motor, it can be rotated freely. The drive member 45 can then be moved manually back to the starting position whereby the plunger rod of each cylinder is pulled outwardly to the fully extended position. Then when the syringe has been refilled with its plunger in the fully extended position, the plunger clamp 51 of the drive member 45 is again clamped over the plunger cap of the plunger rod of the syringe when it is again positioned and clamped in its respective seating recess in the top wall 32 of th syringe pump housing 2. The motor circuit for that particular syringe may then by energized again by moving the motor controller for that circuit back to the "on" position, whereupon the clutch solenoid becomes energized to move the clutch 40 to the engaged position connecting the worm gear 44 of the drive mechanism to the motor at the same time as the motor itself becomes energized and starts rotating.

The variable speed motor controllers 85, 86 and 87 are of conventional type and are able to control the speed of the respective motors 36, 37 and 38 through a range of speeds that will move the drive member 45 of each driving mechanism at whatever rate of out flow desired from each of the respective syringes 3, 4 and 5. For example, the nutritional syringe 3 requires a pump drive mechanism that will feed nutritional elements from syringe 3 at any rate between 0.1 to 99.9 milliliters per hour. Medication syringe 4 requires a pump drive mechanism that will feed medication from syringe 4 at any rate between 0.1 to 5.0 milliliters over periods ranging from five minutes to thirty minutes.

A first flow meter 94 is provided on the top wall 32 of housing 2 to indicate the flow rate per hour of nutritional elements from the nutritional syringe 3, and a second flow meter 95 is also provided thereon to indicate the flow rate per minute of medication from the medication syringe 4.

A first flow rate indicator 96 is provided on the top wall 32 of housing 2 connected to the variable speed motor controller 85 to indicate the setting of such motor controller which will produce the particular flow rate desired from nutritional syringe 3. The flow meter 94 is monitored to see that the desired flow rate is being maintained at that particular setting of the variable speed motor controller 85.

A second flow rate indicator 97 is also provided on the top wall 32 of housing 2, the second flow rate indicator being connected to the variable speed motor controller 86 to indicate the setting of such motor controller which will produce the particular flow rate desired from medication syringe 4. The flow meter 95 is monitored to see that the desired flow rate is being maintained at the particular setting of the variable speed motor controller 86.

The variable speed motor controllers 85, 86 and 87 also include a stop position to completely interrupt the respective motor circuits which energize the motors 36, 37 and 38, to completely stop each respective motor when its controller is moved to the stop position.

The lines leading from the syringe pump 1 and the syringes 3, 4 and 5 mounted therein to the infant who is being fed intravenously are described in detail as follows.

A first length of flexible tubing 98 is connected at one end to the outlet 76 of the nutritional syringe 3, by a coupling member 99. The coupling member 99 includes an inlet port 100 connected to the outlet 76 of the syringe 3, an outlet port 101 connected to the said one end of the flexible tubing 98, and a backfill port 102 extending outwardly from the coupling member 99 between the inlet and outlet ports and at substantially a right angle to those ports.

A gravity bag 103 is provided, having an aperture 104 to receive a hook for holding the bag 103 above the syringe pump, for connection to the backfill port 102 of the coupling member 99 by means of a second length of flexible tubing 105. The gravity bag contains nutrient elements for back feeding into the barrel or cylindrical container 6 of the nutrient syringe 3 after its initial contents have been fed out and its plunger 9 has been pushed fully into the cylindrical container or barrel 6 of the syringe. At such time, the plunger 9 is pulled outwardly creating a vacuum in the cylindrical container 6 thereby drawing nutritional elements from the gravity bag to refill the container 6. The nutritional syringe 3 is then ready for another feeding cycle by moving the variable speed motor controller 85 to the desired flow rate setting which causes motor 36 to operate at the speed necessary to drive the plunger 9 of syringe 3 at the set flow rate feeding nutrient elements through outlet 76 and into the first length of flexible tubing 98.

The other end of flexible tubing 98 is connected to a first inlet port 106 of a Y-shaped connector 107. The Y-shaped connector 107 includes a second inlet port 108 which connects a third length of flexible tubing 109 to coupling 110 attached to the end of outlet 77 of the medication syringe 4.

Coupling 110 includes an inlet port 111 which receives outlet 77, an outlet port 112 which receives an end of the of the third tubing 109, and an auxiliary inlet port 113 extending outwardly from the coupling member 110 between the inlet port 111 and the outlet port 112, and at a substantial right angle thereto. A fourth length of flexible tubing 114 is connected at one end to the auxiliary inlet port 113, and at its other end to the outlet 78 of the flushing syringe 5.

The Y-shaped connector 107 includes a single outlet port 115 in communication with both of its inlet ports 106 and 108. A fifth length of flexible tubing 116 is connected at one end to the outlet port 115 of the Y-shaped connector 107, and this fifth length of tubing 116 leads to the catheter or needle inserted into a vein of the infant who is being fed intravenously.

The syringes 3, 4 and 5 are held in their respective seating recesses 33, 34 and 35 in the top wall 32 of the syringe pump housing 2 by mean of syringe clamps 117, 118 and 119 respectively, which may be unclamped to remove a respective syringe from the pump housing to be refilled or replaced and which may be clamped together to hold the respective syringes firmly in place in their respective seating recesses.

Tube clamps 120, 121 and 122 are provided for the tubes leading from syringes 3, 4 and 5 to clamp the tubes off and keep them closed during any period in which the syringes have been removed. Tube clamp 120 is provided for flexible tube 98 normally connected to syringe 3. Tube clamp 121 is provided for flexible tube 109 normally connected to syringe 4. Tube clamp 122 is provided for flexible tube 114 normally connected to syringe 5.

The syringe clamps 117, 118 and 119 may be connected respectively in syringe clamp alarm circuits 123, 124 and 125, and include syringe clamp switches 126, 127 and 128 respectively which are normally biased to the contact open position when in the clamped position to clamp their respective syringe 3, 4 and 5 in its respective seating recess 33, 34 and 35, and which move to the contact closed position when unclamped. Thus, when clamp 117 for syringe 3 is unclamped, syringe clamp switch 126 is moved to the contact closed position thereby completing syringe clamp alarm circuit 123 causing audible syringe clamp alarm 129 to sound. When clamp 118 for syringe 4 is unclamped, syringe clamp switch 127 is moved to the contact closed position thereby completing syringe clamp circuit 124 which also causes audible syringe clamp alarm 129 to sound. When clamp 119 for syringe 5 is unclamped, syringe clamped switch 128 is moved to the contact closed position thereby completing syringe clamp circuit 125 which causes audible syringe clamp alarm 129 to sound.

Thus, when any one of the syringe clamps 117, 118 or 119 is unclamped, the syringe clamp alarm 129 will sound to alert the attending personnel that when one of the syringes 3, 4 or 5 has been unclamped and is about to be removed, that the respective tube clamp 120, 121 or 122 for the tube connected to whichever one of syringes 3, 4 or 5 is being removed should be clamped to close off the end of such tube. A master clamp alarm switch 130 is provided to interrupt the master clamp alarm circuit 131 which connects the individual syringe clamp alarm circuits 123, 124 and 125 to the battery 39. The master alarm switch 130 is operated manually by a switch operator control on the syringe pump housing 2.

A protective cover 132 is provided to enclose the nutritional syringe 3 when seated in the pump housing 2, and a similar protective cover 133 is provided to cover the medication syringe 4 and flushing syringe 5.

The protective covers 132 and 133 are hingedly connected by respective hinge member 134 and 135 to the syringe pump housing 2, to open and close over the respective syringes 3, 4 and 5 when in their respective seating recesses 33, 34 and 35. The protective covers 132 and 133 are preferably of transparent plastic material.

The protective covers 132 and 133 protect the syringes from exposure to bacteria and other contamination. Since the large nutritional syringe 3 can be refilled by gravity bag 103, it is not necessary to remove this syringe from the syringe pump to refill. The protective cover 132 protects syringe 3 from contamination so it may be refilled and re-used without changing syringes, and without the re-priming and other procedures necessary when the syringe has to be removed for refilling.

I claim:

1. A multiple syringe pump, comprising a pump housing, first seating means of a first size to receive a first syringe therein, second seating means of a second different size to receive a second syringe therein, first drive means connectible to said first syringe to empty its contents at a first independently controlled rate of flow, second drive means connectible to said second syringe to empty its contents at a second independently controlled rate of flow, and control means to independently control said first and second drive means and the flow rate at which each respectively empties the syringe to which is is connected, whereby the said rate of flow from said first syringe may be different than the said rate of flow from said second syringe, said first drive means including a first motor, said second drive means including a second motor, said first motor being operable at one rate of speed, said second motor is operable at a different rate of speed, said first and second motors being operable at the same time to move said drive means in the direction to empty said syringes, and either of said first and second motors being additionally operable while the other is not operating.

2. A multiple syringe pump as set forth in claim 1, including said first and second syringes, said first syringe including a relatively large diameter cylindrical container of relatively long dimension, a piston of corresponding diameter slidably mounted therein for reciprocal movement between a fully inserted position at which point the syringe container is emptied and a fully retracted position at which point the syringe container is filled, a relatively long plunger rod connected to said piston of said first syringe extending outwardly from said cylindrical container thereof, said plunger rod of said first syringe being connectible to said first drive means, said first drive means being operable to drive said plunger rod in a direction to move said piston from said fully retracted position to said fully inserted position at a first rate of travel said second syringe including a relatively small diameter container of relatively short dimension, a piston of corresponding diameter slidably mounted therein for reciprocal movement between a fully inserted position at which the syringe container is emptied and a fully retracted position at which point the syringe container is filled, a relatively short plunger rod connected to said piston of said second syringe extending outwardly from said cylindrical container thereof, said plunger rod of said second syringe being connectible to said second drive means, said second drive means being operable to drive said plunger rod in a direction to move said piston from said fully retracted position to said fully inserted position at a second different rate of travel, said first and second rates of travel being independently determined by said control means.

3. A multiple syringe pump as set forth in claim 2, including a multiple syringe tube connecting member having first and second inlet ports and an outlet port, a first length of flexible tubing connected between said first syringe and said first inlet port of said connecting member, a second length of flexible tubing connected between said second syringe and said second inlet port of said connecting member, and a third length of flexible tubing connected at one end of said outlet port of said connecting member and at the opposite end to means for inserting into the vein of a patient to be fed intravenously.

4. A multiple syringe pump as set forth in claim 3, including a third seating means in said syringe pump housing to receive a third syringe, including said third syringe, said third syringe including a cylindrical container of a diameter smaller than that of said cylindrical container of said first syringe and having a length shorter than that of said container of said first syringe, a piston of corresponding diameter slidably mounted in said cylindrical container of said third syringe for reciprocal movement therein between a fully inserted position at which point said container is emptied and a fully retracted position at which point said container is filled, a plunger rod connected to said piston of said third syringe extending outwardly from said cylindrical container thereof, including third drive means connectible to said third syringe to empty its contents at a third independently controlled rate of flow, said third drive means including a third motor, said control means including means to independently control said third drive means and the flow rate at which said third drive means empties said third syringe at a third different rate of travel, said plunger rod of said third syringe being connectible to said third drive means, said third motor being operable independently of said first and second motors and when said first and second motors are not operating.

5. A multiple syringe pump as set forth in claim 4, including an electrical power source, wherein said first, second and third motors are electric motors, said first drive means includes a first motor circuit powered by said electrical power source, said first electric motor connected in said first motor circuit, a first linear drive mechanism connectible to said first electric motor to drive said plunger rod of said first syringe in a linear direction from the fully retracted position of its piston to the fully inserted position thereof, said second drive means includes a second motor circuit powered by said electrical power source, said second electric motor connected in said second motor circuit, a second linear drive mechanism connectible to said second electric motor to drive said plunger rod of said second syringe in a linear direction from the fully retracted position of its piston to the fully inserted position thereof, said third drive means includes a third motor circuit powered by said electrical power source, said third electric motor connected in said motor circuit, a third linear drive mechanism connectible to said third electric motor to drive said plunger rod of said third syringe in a linear direction from the fully retracted position of its piston to the fully inserted position thereof, said first and second drive mechanisms being operable in the same continuous direction from their fully retracted to their fully inserted positions during the same time periods, said third drive mechanism being operable independently when said first and second drive mechanisms are not operating.

6. A multiple syringe pump as set forth in claim 5, wherein said control means includes a first variable speed motor controller connected in said first motor circuit to control the speed of said first electric motor and accordingly the linear rate of speed of said first linear drive mechanism, a second variable speed motor controller connected in said second motor circuit to control the speed of said second electric motor and accordingly the linear rate of speed of said second linear drive mechanism, and a third variable speed motor controller connected in said third motor circuit to control the speed of said third electric motor and accordingly the linear rate of speed of said third linear drive mechanism, each operable during the same time period to empty said syringes simultaneously at different rates of flow and any one of said first, second and third motors being additionally operable while the others are not operating, the flow rate in each case being constant.

7. A multiple syringe pump as set forth in claim 3, wherein said first and second motors are electric motors, said first drive means includes a first electrical power source, a first motor circuit powered by said first electrical power source, said first electric motor connected in said first motor circuit, a first linear drive mechanism connectible to said first electric motor to drive said plunger rod of said first syringe in a linear direction from the fully retracted position of its piston to the fully inserted position thereof, said second drive means includes a second electrical power source, a second motor circuit powered by said second electrical power source, said second electric motor connected in said second motor circuit, a second linear drive mechanism connectible to said second electric motor to drive said plunger rod of said second syringe in a linear direction from the fully retracted position of its piston to the fully inserted position thereof, said first and second drive means driving said respective plunger rods in the same continuous direction from their fully retracted to their fully inserted positions during the same time periods.

8. A multiple syringe pump as set forth in claim 7, wherein said control means includes a first variable speed motor controller connected in said first motor circuit to control the speed of said first electric motor and accordingly the linear rate of speed of said first linear drive mechanism, and a second variable speed motor controller connected in said second motor circuit to control the speed of said second electric motor and accordingly the linear rate of speed of said second linear drive mechanism, both operable during the same time period to empty said syringes simultaneously at different rates of flow, the flow rate in each case being constant.

9. A multiple syringe pump as set forth in claim 7, including alarm means to indicate when at least one of said respective syringes are empty, comprising a first linear drive member included in said first linear drive mechanism operable for movement in a linear direction from the fully retracted position of the piston of said first syringe to the fully inserted position thereof at which point the syringe is empty, a first syringe-empty alarm circuit in parallel with said first motor circuit, a first syringe-empty audible alarm in said first syringe-empty alarm circuit, a first syringe-empty limit switch in said first syringe-empty alarm circuit positioned for engagement by said first linear drive member when it reaches the position corresponding to the fully inserted position of said piston of said first syringe indicating it is empty to thereupon complete said first syringe-empty alarm circuit thereby energizing said first syringe-empty audible alarm.

10. A multiple syringe pump as set forth in claim 9, including a second linear drive member included in said second linear drive mechanism operable for movement in a linear direction from the fully retracted position of the piston of said second syringe to the fully inserted position thereof at which point the syringe is empty, a second syringe-empty alarm circuit in parallel with said second motor circuit, a second syringe-empty audible alarm in said second syringe-empty alarm circuit, a second syringe-empty limit switch in said second syringe-empty alarm circuit positioned for engagement by said second linear drive member when it reaches the position corresponding to the fully inserted position of said piston of said second syringe indicating it is empty to thereupon complete said second syringe-empty alarm circuit thereby energizing said second syringe-empty audible alarm.

11. A multiple syringe pump as set forth in claim 10, wherein said second syringe-empty limit switch includes a movable contact connected in said second motor circuit, a first stationary contact connected in said second motor circuit, a second stationary contact connected in said second syringe-empty alarm circuit, said movable contact being normally in contact with said first stationary contact to normally complete said second motor circuit, said movable contact being moved into contact with said second stationary contact when said second syringe-empty limit switch is engaged by said second linear drive member and out of contact with said first stationary contact thereby interrupting said second motor circuit stopping said second electric motor and said second linear drive mechanism at the same time as said second syringe-empty alarm circuit and its audible alarm is energized.

12. A multiple syringe pump as set forth in claim 9, wherein said first syringe-empty limit switch includes a movable contact connected in said first motor circuit, a first stationary contact connected in said first motor circuit, a second stationary contact connected in said first syringe-empty alarm circuit, said movable contact being normally in contact with said first stationary contact to normally complete said first motor circuit, said movable contact being moved into contact with said second stationary contact when said first syringe-empty limit switch is engaged by said first linear drive member and out of contact with said first stationary contact thereby interrupting said first motor circuit stopping said first electric motor and said first linear drive mechanism at the same time as said first syringe-empty alarm circuit and its audible alarm is energized.

13. A multiple syringe pump, comprising a pump housing, first seating means to receive a first syringe therein, second seating means to receive a second syringe therein, first drive means connectible to said first syringe to empty its contents at a first independently controlled rate of flow, second drive means connectible to said second syringe to empty its contents at a second independently controlled rate of flow, and control means to independently control said first and second drive means and the flow rate at which each respectively empties the syringe to which it is connected, including said first and second syringes, said first syringe including a relatively large diameter cylindrical container of relatively long dimension, a piston of corresponding diameter slidably mounted therein for reciprocal movement between a fully inserted position at which point the syringe container is emptied and a fully retracted position at which point the syringe container is filled, a relatively long plunger rod connected to said piston of said first syringe extending outwardly from said cylindrical container thereof, said plunger rod of said first syringe being connectible to said first drive means, said first drive means being operable to drive said plunger rod in a direction to move said piston from said fully retracted position to said fully inserted position, said second syringe including a relatively small diameter container of relatively short dimension, a piston of corresponding diameter slidably mounted therein for reciprocal movement between a fully inserted position at which the syringe container is emptied and a fully retracted position at which point the syringe container is filled, a relatively short plunger rod connected to said piston of said second syringe extending outwardly from said cylindrical container thereof, said plunger rod of said second syringe being connectible to said second drive means, said second drive means being operable to drive said plunger rod in a direction to move said piston from said fully retracted position to said fully inserted position, including a multiple syringe tube connecting member having first and second inlet ports and an outlet port, a first length of flexible tubing connected between said first syringe and said first inlet port of said connecting member, a second length of flexible tubing connected between said second syringe and said second inlet port of said connecting member, and a third length of flexible tubing connected at one end to said outlet port of said connecting member and at the opposite end to means for inserting into the vein of a patient to be fed intravenously, including a third seating means in said syringe pump housing to receive a third syringe, including said third syringe, said third syringe including a cylindrical container of a diameter smaller than that of said cylindrical container of said first syringe and having a length shorter than that of said container of said first syringe, a piston of corresponding diameter slidably mounted in said cylindrical container of said third syringe for reciprocal movement therein between a fully inserted position at which point said container is emptied and a fully retracted position at which point said container is filled, a plunger rod connected to said piston of said third syringe extending outwardly from said cylindrical container thereof, including third drive means connectible to said third syringe to empty its contents at a third independently controlled rate of flow, said control means including means to independently control said third drive means and the flow rate at which said third drive means empties said third syringe, said plunger rod of said third syringe being connectible to said third drive means, wherein said first syringe includes a first outlet connector having a primary inlet port connected to the discharge end of said first syringe, an outlet port of said first outlet connector connected to said first length of flexible tubing, and an auxiliary inlet port of said first outlet connector, a gravity bag for positioning above said first syringe for backfilling thereof, a fourth length of flexible tubing connected between said gravity bag and said auxiliary inlet port of said first outlet connector of said first syringe.

14. A multiple syringe pump as set forth in claim 13, wherein said second syringe includes a second outlet connector having a primary inlet port connected to the discharge end of said second syringe, an outlet port of said second outlet connector connected to said second length of flexible tubing, and an auxiliary inlet port of said second outlet connector, a fifth length of flexible tubing connected between said third syringe and said auxiliary inlet port of said second outlet connector of said second syringe.

15. A multiple syringe pump, comprising a pump housing, first seating means to receive a first syringe therein, second seating means to receive a second syringe therein, first drive means connectible to said first syringe to empty its contents at a first independently controlled rate of flow, second drive means connectible to said second syringe to empty its contents at a second independently controlled rate of flow, and control means to independently control said first and second drive means and the flow rate at which each respectively empties the syringe to which it is connected, including said first and second syringes, said first syringe including a relatively large diameter cylindrical container of relatively long dimension, a piston of corresponding diameter slidably mounted therein for reciprocal movement between a fully inserted position at which point the syringe container is emptied and a fully retracted position at which point the syringe container is filled, a relatively long plunger rod connected to said piston of said first syringe extending outwardly from said cylindrical container thereof, said plunger rod of said first syringe being connectible to said first drive means, said first drive means being operable to drive said plunger rod in a direction to move said piston from said fully retracted position to said fully inserted position, said second syringe including a relatively small diameter container of relatively short dimension, a piston of corresponding diameter slidably mounted therein for reciprocal movement between a fully inserted position at which the syringe container is emptied and a fully retracted position at which point the syringe container is filled, a relatively short plunger rod connected to said piston of said second syringe extending outwardly from said cylindrical container thereof, said plunger rod of said second syringe being connectible to said second drive means, said second drive means being operable to drive said plunger rod in a direction to move said piston from said fully retracted position to said fully inserted position, including a multiple syringe tube connecting member having first and second inlet ports and an outlet port, a first length of flexible tubing connected between said first syringe and said first inlet port of said connecting member, a second length of flexible tubing connected between said second syringe and said second inlet port of said connecting member, and a third length of flexible tubing connected at one end to said outlet port of said connecting member and at the opposite end to means for inserting into the vein of a patient to be fed intravenously, wherein said first drive means includes a first electrical power source, a first motor circuit powered by said first electrical power source, including a first electric motor connected in said first motor circuit, a first linear drive mechanism connectible to said first electric motor to drive said plunger rod of said first syringe in a linear direction from the fully retracted position of its piston to the fully inserted position thereof, said second drive means includes a second electrical power source, a second motor circuit powered by said second electrical power source, including a second electric motor connected in said second motor circuit, a second linear drive mechanism connectible to said second electric motor to drive said plunger rod of said second syringe in a linear direction from the fully retracted position of its piston to the fully inserted position thereof, including first alarm means to indicate when at least one of said respective syringes are near the empty mark but at a preselected mark before empty, comprising a first linear drive member included in said first linear drive mechanism operable for movement in a linear direction from the fully retracted position of the piston of said first syringe to a preselected position of such piston before it reaches the empty position thereof, a first alarm circuit connected in parallel with said first motor circuit, a first audible alarm in said first alarm circuit, a normally open first before-empty limit switch in said first alarm circuit, said first before-empty limit switch being positioned for engagement by said first linear drive member when it reaches said position corresponding to said preselected position of said piston of said first syringe before it reaches the empty position thereof whereupon said first before-empty limit switch is moved to the closed position to complete said first alarm circuit and energize said first audible alarm.

16. A multiple syringe pump as set forth in claim 15, including a second linear drive member included in said second linear drive mechanism operable for movement in a linear direction from the fully retracted position of the piston of said second syringe to a preselected position of such piston before it reaches the empty position thereof, a second alarm circuit connected in parallel with said second motor circuit, a second audible alarm in said second alarm circuit, a normally open second before-empty limit switch in said second alarm circuit, said second before-empty limit switch being positioned for engagement by said second linear drive member when it reaches said position corresponding to said preselected position of said piston of said second syringe before it reaches the empty position thereof whereupon said second before-empty limit switch is moved to the closed position to complete said second alarm circuit and energize said second audible alarm.

* * * * *